US005571713A

United States Patent [19]
Lyle et al.

[11] Patent Number: 5,571,713
[45] Date of Patent: Nov. 5, 1996

[54] THERAPEUTIC TREATMENT FOR INHIBITING VASCULAR RESTENOSIS

[75] Inventors: Leon R. Lyle, Webster Groves, Mo.; Steven L. Kunkel; Robert M. Strieter, both of Ann Arbor, Mich.

[73] Assignee: The Regents of the University of Michigan, Ann Arbor, Mich.

[21] Appl. No.: 250,958

[22] Filed: May 27, 1994

Related U.S. Application Data

[63] Continuation-in-part of Ser. No. 965,678, Oct. 22, 1992, abandoned.

[51] Int. Cl.$^6$ .............................. C12N 5/10; C12N 5/08; C07H 21/04; C07H 21/02
[52] U.S. Cl. ................. 435/240.2; 536/24.5; 536/24.31; 536/24.33; 536/26.1
[58] Field of Search .............................. 536/24.5, 24.31, 536/24.33, 26.1; 514/44; 435/240.2, 6

[56] References Cited

U.S. PATENT DOCUMENTS

| | | | |
|---|---|---|---|
| 4,276,280 | 6/1981 | Akerkar et al. | 424/1 |
| 4,520,112 | 5/1985 | Snyder et al. | 436/504 |
| 4,656,280 | 4/1987 | Garlick | 546/20 |
| 4,659,839 | 4/1987 | Nicolotti et al. | 548/546 |
| 4,732,974 | 3/1988 | Nicolotti et al. | 530/390 |
| 4,832,940 | 5/1989 | Ege | 424/1.1 |
| 4,837,003 | 6/1989 | Nicolotti | 424/1.1 |
| 4,926,869 | 5/1990 | Rubin et al. | 128/654 |
| 4,965,392 | 10/1990 | Fritzberg et al. | 558/254 |
| 4,986,979 | 1/1991 | Morgan, Jr. et al. | 424/1.1 |
| 5,037,630 | 8/1991 | Fritzberg et al. | 424/1.1 |
| 5,079,228 | 1/1992 | Cohen et al. | 514/12 |
| 5,120,525 | 6/1992 | Goldenberg | 424/1.1 |
| 5,179,078 | 1/1993 | Rollins et al. | 514/2 |
| 5,196,510 | 3/1993 | Rodwell et al. | 530/324 |
| 5,198,424 | 3/1993 | McEver | 514/13 |
| 5,225,180 | 7/1993 | Dean et al. | 424/1.1 |
| 5,241,049 | 8/1993 | Goodman et al. | 530/350 |

FOREIGN PATENT DOCUMENTS

| | | |
|---|---|---|
| 0284071 | 9/1988 | European Pat. Off. |
| 0398143 | 11/1990 | European Pat. Off. |
| 9002762 | 3/1990 | WIPO |
| 9013317 | 11/1990 | WIPO |
| 9116919 | 11/1991 | WIPO |
| 9204372 | 3/1992 | WIPO |

OTHER PUBLICATIONS

J. Wang et al., "Human Recombinant Macrophage Inflammatory Protein–1α and –β and Monocyte...", J. Immunol., vol., 150, No. 7, pp. 3022–3029, (Apr. 1, 1993).
A. K. Samanta et al., "Interleukin 8 (Monocyte–derived Neutrophil Chemotactic Factor)...", J. Biol. & Chem., vol. 285, No. 1, pp. 183–189, (Jan. 6, 1990).
Schitzel, W., et al., "Neutorphil Activating Peptide–2 Binds with Two Affinities to...", Biochem. & Biophys. Res. Comm., vol. 1, No. 1, pp. 301–307, (Oct. 15, 1991).
Horuk, R., et al., "Purification, Receptor Binding Analysis...", Journ. Biolog. Chem., vol. 268, No. 1, pp. 541–546 (Jan. 5, 1993).
Neote, K., et al., "Identification of a Promiscuous Inflammatory...", Journ. Biolog. Chem., vol. 268, No. 17, pp. 12247–12249, (Jun. 15, 1993).
Besemer, J., et al., "Specific Binding, Internalization, and Degradation of Human...", Journ. Biolog. Chem., vol. 264, No. 29, pp. 17409–17415, (Oct. 15, 1989).
Elner, V. M., et al., "Rapid Communication...", Amer. Journ. Pathol., vol. 136, No. 4, pp. 745–750, (Apr. 1990).
Standiford, T. J., et al., "Disparate Regulation of Interleukin 8 Gene Expression From Blood...", Biochem. & Biophys. Res. Comm., vol. 171, No. 2, pp. 531–536, (Sep. 14, 1990).
Thornton, A. J., et al., "Cytokine–Induced Gene Expression...", J. Immuno., vol. 144, No. 7, pp. 2609–2613, (Apr. 1, 1990).
Samanta, A. K., et al., "Identification and Characterization of Specific Receptors for...", J. Exper. Med., vol. 169, pp. 1185–1189, (Mar. 1989).
Hebert, C. A., et al., "Endothelial and Leukocyte Forms of IL–8...", J. Immuno., vol. 145, No. 9, pp. 3033–3040, (Nov. 1, 1990).
Darbonne, W. C., et al., "Red Blood Cells Are a Sink for Interleukin 8, a Leukocyte Chemotaxin", J. Clin. Invest., vol. 88, pp. 1362–1369, (Oct. 1991).
Ross, R., "Medical Progress: The Pathogenesis of Atherosclerosis...", New Eng. J. of Med., vol. 314, No. 8, pp. 488–500, (Feb. 20, 1986).
Grob, P. M., et al., "Characterization of a Receptor for Human Monocyte–derived...", J. Biolog. Chem., vol. 265, No. 14, pp. 8311–8316, (May 15, 1990).
Clark-Lewis, I., et al., "Platelet factor 4 binds to interleukin 8...", Proc. Natl. Acad. Sci., vol. 90, pp. 3574–3577, (Apr. 1993).
Rot. Antal, "Binding of Neutrophil Attractant/Activation Protein–1...", Chemical Abstracts, vol. 119, No. 21, (Nov. 22, 1993) and Cytokine, vol. 4, No. 5, pp. 347–352, (1992). Abstract.
Vita, N., et al., "Functional Linkage of the Gro.Beta and IL–8 Receptors on the Surface...", Chemical Abstracts, vol. 120, No. 9, and Eur. Cytokine Network, vol. 4, No. 3, pp. 197–204, (1993). Abstract.
Uhlmann, E. et al. "Antisense Oligonucleotides: A New Therapeutic Principle" Chemical Reviews 90(4) 543–584 (Jun. 1990).
Souza, S. J. U. and Bretani, R. J., Biol. Chem. 267:13763–13773 (1992).

*Primary Examiner*—Charles C. P. Rories
*Attorney, Agent, or Firm*—Rothwell, Figg, Ernst & Kurz

[57] ABSTRACT

A composition suitable for administration to a warm-blooded animal comprising antisense MCP-1 peptide or oligonucleotide or a molecule capable of interacting with MCP-1 peptide or information for its synthesis which may or may not be labeled with a radionuclide by means of a chelate ligand capable of administration to an animal to produce reliable visual imaging of areas of potential restenosis or to produce therapeutic effects on areas of areas of potential restenosis.

7 Claims, 6 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 76 amino acids
( B ) TYPE: amino acid
( C ) STRANDEDNESS:
( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

```
Gly Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75
```

( 2 ) INFORMATION FOR SEQ ID NO:2:

( i ) SEQUENCE CHARACTERISTICS:
( A ) LENGTH: 76 amino acids
( B ) TYPE: amino acid
( C ) STRANDEDNESS: Not Relevant
( D ) TOPOLOGY: linear ( i i ) MOLECULE TYPE: peptide ( i i i ) HYPOTHETICAL: NO ( i v ) ANTI-SENSE: YES ( v ) FRAGMENT TYPE: N-terminal ( x i ) SEQUENCE DESCRIPTION: SEQ ID NO:2:

```
Xaa Gly Leu Arg Xaa Leu Arg Gly Xaa Xaa Thr Thr Xaa Leu Lys Xaa
 1               5                  10                  15

Leu Xaa Phe Xaa Xaa Xaa Val Xaa Xaa Arg Xaa Xaa Xaa Xaa Xaa Xaa
            20                  25                  30

Xaa Xaa Phe Thr Gly Phe Leu Arg Xaa Xaa Lys Phe Xaa Xaa Xaa Arg
        35                  40                  45

Phe Leu Xaa Thr Arg Leu Gly Phe Val Phe Thr Xaa Val Leu Xaa Tyr
```

| | 50 | | | | 55 | | | | 60 | |
|---|---|---|---|---|---|---|---|---|---|---|
| Leu | Val | Xaa | Leu | Phe | Val | Xaa | Val | Xaa | Gly | Phe | Xaa |
| 65 | | | | | 70 | | | | | 75 |

( 2 ) INFORMATION FOR SEQ ID NO:3:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:3:

| CAGCCAGAUG | CAAUCAAUGC | CCAGUCACC | UGCUGUUAUA | ACUUCACCAA | UAGGAAGAUC | 60 |
|---|---|---|---|---|---|---|
| UCAGUGCAGA | GGCUCGCGAG | CUAUAGAAGA | AUCACCAGCA | GCAAGUGUCC | CAAAGAAGCU | 120 |
| GUGAUCUUCA | AGACCAUUGU | GGCCAAGGAG | AUGUGUGCUG | ACCCCAAGCA | GAAGUGG GUU | 180 |
| CAGGAUUCCA | UGCACCACCU | GGACAAGCAA | ACCCAAACUC | CGAAGACU | | 228 |

( 2 ) INFORMATION FOR SEQ ID NO:4:

( i ) SEQUENCE CHARACTERISTICS:
        ( A ) LENGTH: 228 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

| GTCGGTCTAC | GTTAGTTACG | GGGTCAGTGG | ACGACA ATAT | TGAAGTGGTT | ATCCTTCTAG | 60 |
|---|---|---|---|---|---|---|
| AGTCACGTCT | CCGAGCGCTC | GATATCTTCT | TAGTGGTCGT | GGTTCACAGG | GTTTCTTCGA | 120 |
| CACTAGAAGT | TCTGGTAACA | CGGGTTCCTC | TAGACACGAC | TGGGGTTCGT | CTTCACCCAA | 180 |
| GTCGTAAGGT | ACCTGGTGGA | CCTGTTCGTT | TGGGTTTGAG | GCTTCTGA | | 228 |

( 2 ) INFORMATION FOR SEQ ID NO:5:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: YES ( x i ) SEQUENCE DESCRIPTION: SEQ ID NO:5:

| GUCGGUCUAC | GUUAGUUACG | GGGUCAGUGG | ACGACAAUAU | UGAAGUGGUU | AUCCUUCUAG | 60 |
|---|---|---|---|---|---|---|
| AGUCACGUCU | CCGAGCGCUC | GAUAUCUUCU | UAGUGGUCGU | CGUUCACAGG | GUUUCUUCGA | 120 |
| CACUAGAAGU | UCUGGUAACA | CCGGUUCCUC | UAGACACGAC | UGGGGUUCGU | CUUCACCCAA | 180 |
| GUCCUAAGGU | ACCUGGUGGA | CCUGUUCGUU | UGGGUUUGAG | GCUUCUGA | | 228 |

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="ANTISENSE RNA CONTRUCT"

( i i i ) HYPOTHETICAL: NO ( i v ) ANTI-SENSE: YES ( x i ) SEQUENCE DESCRIPTION: SEQ ID NO:6:

CAGUGGAGCA CAAUAUUG                                                                                        18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="ANTISENSE DNA CONSTRUCT"

( i i i ) HYPOTHETICAL: NO ( i v ) ANTI-SENSE: YES ( x i ) SEQUENCE DESCRIPTION: SEQ ID NO:7:

CAGTGGAGCA CAATATTG                                                                                        18

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="OLIGONUCLEOTIDE"

( i i i ) HYPOTHETICAL: NO ( i v ) ANTI-SENSE: YES ( x i ) SEQUENCE DESCRIPTION: SEQ ID NO:8:

ACTTCTGCTT GGGGTCAGCA CAGATCTCC                                                                             29

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="OLIGONUCLEOTIDE"

( i i i ) HYPOTHETICAL: NO ( i v ) ANTI-SENSE: YES ( x i ) SEQUENCE DESCRIPTION: SEQ ID NO:9:

GCTTCAGTTT GAGAATTGGA TGTTTCTGG                                                                             29

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="OLIGONUCLEOTIDE"

( i i i ) HYPOTHETICAL: NO ( i v ) ANTI-SENSE: YES ( x i ) SEQUENCE DESCRIPTION: SEQ ID NO:10:

AAGCGTGACA GAGACCTGCA TAGTGGTGG        29

THERAPEUTIC TREATMENT FOR INHIBITING VASCULAR RESTENOSIS

This application is a continuation-in-part of U.S. application Ser. No. 07/965,678, filed Oct. 22, 1992, now abandoned.

FIELD OF THE INVENTION

This invention relates generally to novel compounds for therapeutic use, and more particularly, to specific molecularly interactive compounds, to methods of preparing and using such specific compounds, and to pharmaceutical compositions comprising these specific compounds for therapeutic use in areas of vascular injury, sites of inflammation, vascular atheromatous disease and/or restenosis.

BACKGROUND OF THE INVENTION

Balloon angioplasty, atherectomy, rotorary ablation and similar therapeutic techniques used to improve circulation in vivo are finding ever-increasing application in therapeutic cardiology. Generally, balloon angioplasty procedures involve the introduction of a balloon-type catheter into the narrowed portion of an artery. The narrowing of the artery may be caused by different factors but most commonly is caused by a build-up of "atherosclerotic plaque". Once the catheter is positioned in the narrowed portion of the artery, the balloon portion of the catheter is inflated. The inflation of the balloon within the narrowed area of the artery serves to increase the diameter of the blood vessel thus improving circulation.

Often times, following a balloon angioplasty therapeutic procedure or similar therapeutic technique with attendant vascular injury, patients experience a re-narrowing or restenosis, of the artery within six months after having undergone the angioplasty therapeutic treatment or after incurring the particular vascular injury. Restenosis is of considerable concern since its effects may be life threatening.

Therefore, the need for a suitable compound for therapeutic use to prevent restenosis following balloon angioplasty or similar therapeutic techniques which may cause vascular injury is of significant importance. It is an object of the present invention to meet this need.

SUMMARY OF THE INVENTION

The present invention discloses novel peptide, polypeptide and oligonucleotide compounds, methods of preparing these compounds, pharmaceutical compositions comprising these compounds and the use of these compounds in balloon-type catheters for therapeutic treatment to inhibit vascular restenosis. Restenosis is a recurrent stenosis, i.e., a narrowing or stricture of a duct or canal. Restenosis and the development of atheromatous lesions (the reason for the procedure in the first place) share several common pathological elements such as the accumulation of monocytes and macrophages at the area of injury or inflammation and the proliferation of vascular smooth muscle. Growth factors which induce this proliferation of vascular smooth muscle and thus cause restenosis, arise from the monocytes and macrophages which infiltrate the injured area in response to inflammatory stimuli. The monocytes and macrophages present in the tissue represent stages of differentiation of the same cell lineage. The cells are referred to as monocytes when in the blood. Upon deposition in tissue, the cells are called macrophages.

Monocyte Chemotactic Protein-1, hereinafter referred to as "MCP-1" is a member of the "C—C" family of chemokines. It is a potent stimulator of monocyte chemotaxis and has an extremely high degree of specificity for this cell type. Other family members include Human Macrophage Inflammatory Protein-1 (HuMIP-1) alpha and beta, Monocyte Chemotactic Protein-2 (MCP-2), RANTES and 1-309. All of these cytokines incorporate a cysteine cysteine (CC) motif, but MCP-1 is the one most highly specific for monocytes and macrophages. MCP-1 is produced by injured vascular smooth muscle cells. The MCP-1 so produced attracts the monocytes and macrophages which infiltrate the area releasing growth factors and resulting in proliferation of vascular smooth muscle and restenosis.

In using a molecularly interactive therapeutic compound to inhibit vascular restenosis as discussed herein, the compound must be highly selective. High selectivity, which is essential in such therapeutic compounds, means that the compound, after having been introduced into the body, accumulates to a greater degree in the target tissue or tissues, i.e. the area of possible restenosis, than in surrounding tissues. In using peptides, polypeptides or oligonucleotides as therapeutic compounds, the specific high selectivity of the particular agent used provides for the strong accumulation of the therapeutic compound in the specific tissue or tissues targeted. In the case of the present invention, the site of accumulation is in areas of injured vascular smooth muscle cells as compared with the accumulation and concentration thereof in other non-target tissues.

DETAILED DESCRIPTION OF THE INVENTION

Figure 1:
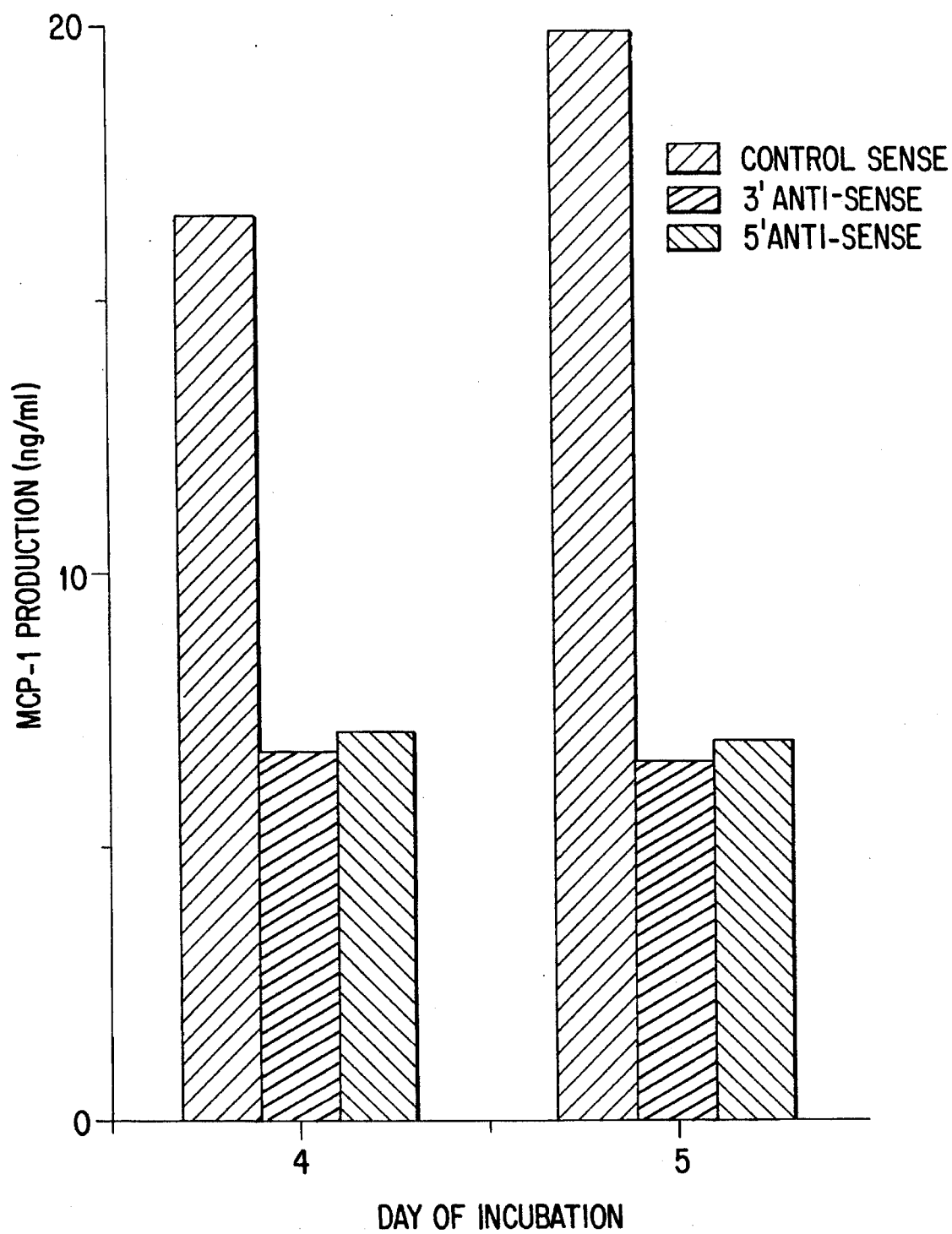
FIG. 1 is a graph showing MCP-1 production with and without the presence of MCP-1 antisense oligonucleotidesto MCP-1.

In the present invention, a balloon-type catheter such as a balloon infusion catheter is coated or filled with a total, partial or synthetic antisense peptide or oligonucleotide to a monocyte chemoattractant protein (MCP) material, such as monocyte chemoattractant protein-1 (MCP-1), a member of the CC family of chemotactic cytokines or chemokines hereinafter referred to as "antisense MCP-1". An antisense peptide is specified by the DNA strand complementary to that which specifies the ordinary sense peptide. These antisense peptides function by "hydropathic complememtarity"

to give binding activity with its corresponding sense peptides and can function as receptor like molecules in affinity chromatography as explained by Souza, S. J. U. and Bretani, R. J., Biol. Chem. 267: 13763–13773 (1992). When an antisense peptide is used, one obtains complementary binding to and inactivation of the mature MCP-1 polypeptide. When an antisense oligonucleotide is used, this antisense oligonucleotide to MCP-1 inhibits the translation or transcription of MCP-1 mRNA within the vascular smooth muscle cells or surrounding interstitial space. Accordingly, MCP-1 production is severely inhibited. In the absence of MCP-1, monocytes are not attracted to the area of vascular injury in their usual numbers. As a result of the monocytes not infiltrating the area, growth factors (GFs) are not released. The relative lack of GFs does not support the proliferation of vascular smooth muscle cells which cause restenosis in cases of vascular injury.

Therapeutic treatment of vascular restenosis can also be achieved and augmented through the use of another embodiment of the present invention whereby the antisense MCP-1 polypeptide or oligonucleotide is labelled with a radionuclide for therapeutic use. Radiolabelled antisense MCP-1 compounds for therapeutic use may be constructed using high energy alpha or beta emitting isotopes rather than the pure gamma emitters customarily used for diagnostic purposes which is also possible and will be discussed in more detail below.

The sense MCP-1 polypeptide sequence having sequence identification No. 1 (SEQ ID NO 1) is as follows:

NH$_2$-G P D A I N A P V T C C Y N F T N R K I S V Q
R L A S Y R R I T S S K C P K E A V I F K T I V A
K E I C A D P K Q K W V Q D S M D H L D K Q
T Q T P K T-COOH wherein A represents Alanine, B represents Asparagine or Aspartic Acid, C represents Cysteine, D represents Aspartic Acid, E represents Glutamic Acid, F represents Phenylalanine, G represents Glycine, H represents Histidine, I represents Isoleucine, K represents Lysine, L represents Leucine, M represents Methionine, N represents Asparagine, P represents Proline, Q represents Glutamine, R represents Arginine, S represents Serine, T represents Threonine, V represents Valine, W represents Tryptophan, X represents an unspecified or variable amino acid, Y represents Tyrosine and Z represents Glutamine Acid.

The antisense MCP-1 (SEQ ID NO 2) of the present invention having sequence identification No. 2 is represented by the following sequence:

NH$_2$ X G L R X L R G X X T T X L K X L X F X X X
V X X R X X X X X X X X F T G F L R X X K F X X
X R F L X T R L G F V F T X V L X Y L V X L F V X
V X G F X COOH

The oligonucleotides in the messenger ribonucleic acid (mRNA), antisense deoxyribonucleic acid (DNA) and antisense RNA corresponding to mRNA sequences for MCP-1 are as follows.

mRNA:
5'-CAG CCA GAU GCA AUC AAU GCC CCA GUC
ACC UGC UGU UAU AAC UUC ACC AAU AGG
AAG AUC UCA GUG CAG AGG CUC GCG AGC
UAU AGA AGA AUC ACC AGC AGC AAG UGU
CCC AAA GAA GCU GUG AUC UUC AAG ACC
AUU GUG GCC AAG GAG AUG UGU GAC
CCC AAG CAG AAG UGG GUU CAG GAU UCC
AUG GAC CAC CUG GAC AAG CAA ACC CAA
ACU CCG AAG ACU -3' (SEQ ID NO:3);
Antisense DNA: 5'-GTC GGT CTA CGT TAG TTA CGG
GGT CAG TGG ACG ACA ATA TTG AAG TGG TTA TCC
TTC TAG AGT CAC GTC TCC GAG CGC TCG ATA TCT
TCT TAG TGG TCG TGG TTC ACA GGG TTT CTT CGA
CAC TAG AAG TTC TGG TAA CAC GGG TTC CTC TAG
ACA CGA CTG GGG TTC GTC TTC ACC CAA GTC GTA
AGG TAC CTG GTG GAC CTG TTC GTT TGG GTT TGA
GGC TTC TGA -3' (SEQ ID NO:4); and
Antisense RNA:
5'-GUC GGU CUA CGU UAG UUA CGG GGU CAG
UGG ACG ACA AUA UUG AAG UGG UUA UCC
UUC UAG AGU CAC GUC UCC GAG CGC UCG
AUA UCU UCU UAG UGG UCG UGG UUC ACA
GGG UUU CUU CGA CAC UAG AAG UUC UGG
UAA CAC CGG UUC CUC UAG ACA CGA CUG
GGG UUC GUC UUC ACC CAA GUC CUA AGG
UAC CUG GUG GAC CUG UUC GUU UGG GUU
UGA GGC UUC UGA -3' (SEQ ID NO:5);

wherein A=Adenine, T=Thymine, C=Cytosine, G=Guanine, U=Uracil, B=not A, D=not C, F=not G, K=G or T, M=A or C, N=A, C, G or T, R=A or G, S=C or G, V=not T, W=A or T and Y=C or T.

In targeting mature MCP-1 polypeptide with antisense MCP-1 polypeptide, it is not necessary that the complete seventy-six (76) residue sequence be present. Effective complementary binding may reside in a smaller portion of the molecule. Through substitution in the antisense MCP-1 polypeptide sequence, and perhaps incorporating (d) amino acid enantiomorphs, retroinverse bonds and the like, additional useful peptides are developed without affecting complementary binding specificity and affinity desired.

Similarly in targeting oligonucleotides into smooth muscle cells it is not necessary that the entire oligonucleotide sequence be present. It is also useful to replace some oxygen atoms in the phosphate backbone with thiol groups to inhibit degradation in vivo.

In the present invention, the antisense MCP-1 polypeptide or oligonucleotide or a molecule having similar specificity, may be administered in vivo using a balloon infusion catheter with holes in it for delivery to the particular target site to prevent life-threatening restenosis. The antisense MCP-1 polypeptide or oligonucleotide may also be radiolabelled prior to administration, using more than one method. The objective in radiolabeling is to increase therapeutic effect by bringing this cytotoxic properly to bear upon smooth muscle. The reaction in radiolabelling peptides generally takes place between the amino groups in the peptide and the carbonyl group in the active ester of a specific ligand to form an amide bond. In particular, the peptides can be radiolabelled using either a conventional method referred to as "post-formed chelate approach" or by a recent method referred to as "pre-formed chelate approach" developed by Fritzberg et al., U.S. Pat. Nos. 4,965,392 and 5,037,630 incorporated herein by reference. In the "pre-formed approach," the desired ligand is complexed with the radionuclide and then conjugated to antisense MCP-1 polypeptide or a molecule having antisense MCP-1 activity. In the "post-formed approach," the desired ligand is first conjugated to the antisense peptide and the resulting conjugate is incubated with the radionuclide along with a reducing agent. In the present invention, the latter approach has the additional advantage of allowing preparation of the complex in kit form. Users merely add the radionuclide to the ligand antisense MCP-1 conjugate or a derivative thereof for labelling to occur.

It is important to note an unique mechanism of the present invention whereby the conjugation reaction will only occur when the amino group is in the "free base" form, i.e., deprotonated to the NH$_2$ form. If the amino group is protonated, i.e., in the $NH_2^+$ form, the reaction will not occur. Therefore, in the molecules of the present invention it is potentially important to perform the conjugation at neutral pH or within the range of 7.0 to 9.5 to avoid deprotonation of epsilon-amino groups of lysine, or K. Avoiding the deprotonation of epsilon-amino groups involved in binding prevents the formation of a chelate complex which may interfere with the ability of the peptide to form a complementary complex with MCP-1. In the present invention, binding preferably occurs on the alpha amino group in order to avoid potential interference with the ability of the antisense MCP-1 peptide to form a complementary complex with sense.

Using either method of labelling antisense MCP-1, any suitable ligand can be used to incorporate the preferred radionuclide metal ion such as for example but not limited to technetium, rhenium, indium, gallium, samarium, holmium, yttrium, copper, or cobalt, and more particularly, yttrium-90, rhenium-188, rhenium-186, indium-111, technetium$^{-99m}$, and derivatives thereof. The choice of the ligand entirely depends on the type of metal ion desired for therapeutic or even diagnostic purposes. For example, if the radionuclide is a transition element such as technetium or rhenium, then ligands containing amine, amide, and thiols are preferred to form a stable complex whereas if the radionuclide is a lanthanide element, then polyaminocarboxyates or phenolate type ligands are preferable.

The above-described unique characteristics of the present invention make the radiolabelled antisense MCP-1 polypeptide and its derivatives very attractive for therapeutic purposes or even diagnostic uses to identify sites of restenosis and/or vascular injury. The compounds of the present invention may be labelled with any radionuclide favorable for these purposes. Such suitable radionuclides for radiotherapy include but are not limited to rhenium-186, copper-67, rhenium-188 and cobalt-60. For diagnostic purposes the most suitable radionuclides include but are not limited to the transition metals as exemplified by technetium-99m and copper-62.

Due to the unique mechanism employed in the present invention to label the alpha amino group of antisense MCP-1 and avoid the epsilon amino group(s) (which could inhibit the ability of antisense MCP-1 peptides to bind to its complementary sense strand) a significantly advantageous radiolabelled peptide compound for radiotherapy and diagnostic imaging of areas of potential restenosis is achieved.

As previously noted, the preferred embodiment of the present invention is the peptide, polypeptide or protein antisense MCP-1 or derivatives thereof used alone to prevent vascular restenosis. However, additional embodiments of the present invention include antisense MCP-1 or derivatives thereof radiolabelled using a pre-formed or post-formed methodology.

In a preferred embodiment according to the present invention, antisense MCP-1 or a molecule having sense MCP-1 interactive capability is first bonded to the $N_2S$ aminothiol ligand which is illustrated in FIG. 1

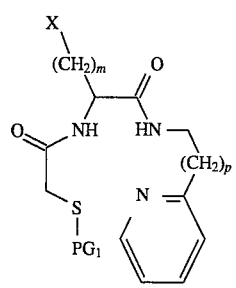

FIG. 1 wherein m is a whole number less than eleven and preferably 3; p is either 0 or 1; $PG_1$ is a suitable sulfur protecting group selected from the group consisting of $C_{1-20}$S-acyl such as alkanoyl, benzoyl and substituted benzoyl—whereby alkanoyl is preferable, $C_{1-20}$S-acyl groups such as benzyl, t-butyl, trityl, 4-methoxybenzyl and 2,4-dimethoxybenzyl—whereby 2,4-dimethoxybenzyl is preferable, $C_{1-10}$ alkoxyalkyl such as methoxymethyl, ethoxyethyl and tetrahydropyranyl—whereby tetrahydropyranyl is preferable, carbamoyl, and $C_{1-10}$ alkoxycarbonyl such as t-butoxycarbonyl and methoxycarbonyl—whereby t-butoxycarbonyl is preferable; and X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl and $C_{1-10}$ N-alkoxycarbamoyl—whereby N-methoxylcabamoyl is preferable.

Figure 2:
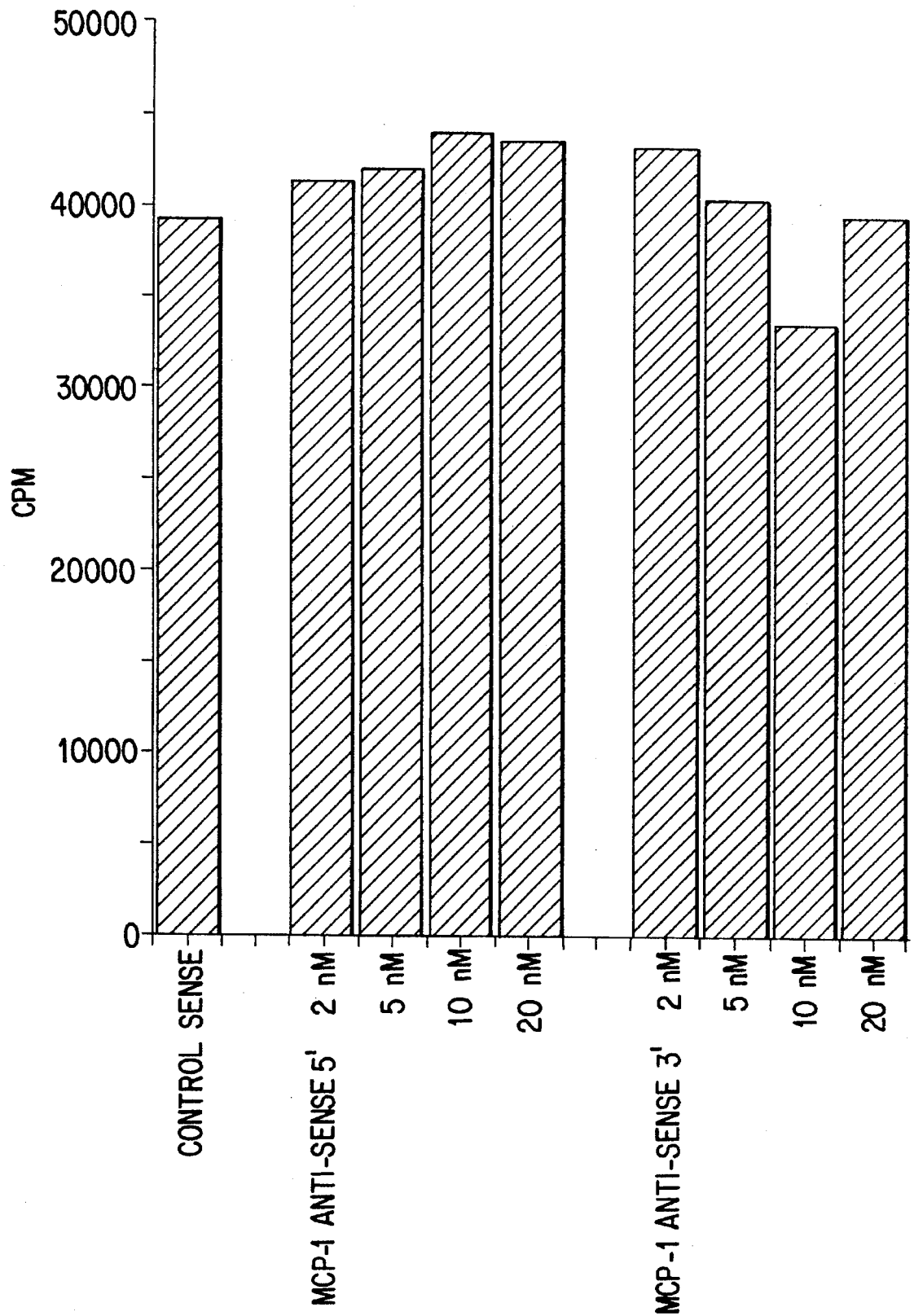
FIG. 2 is a graph showing impact on MLR proliferative response using antisense oligonucleotidesto MCP-1 treatment.

In another preferred embodiment according to the present invention, antisense MCP-1 or a molecule having sense MCP-i interactive capability is bonded to the $N_2S_2$ aminothiol ligand which is illustrated in FIG. 2;

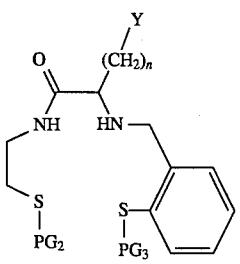

FIG. 2 wherein n is a whole number less than eleven and preferably 3; $PG_2$ and $PG_3$ may be the same or different sulfur protecting groups selected from the group consisting of $C_{1-20}$ S-acyl such as alkanoyl, benzoyl and substituted benzoyl—whereby alkanoyl is preferable, $C_{1-20}$ alkyl groups such as benzyl, t-butyl, 4-methoxbenzyl, trityl and 2,4-dimethoxbenzyl—whereby 2,4-dimethoxbenzyl is preferable, $C_{1-10}$ alkoxalkyl such as for example methoxymethyl, ethoxyethyl, and tetrahydropyranyl—whereby tetrahdropyranyl is preferable, carbamoyl and $C_{1-10}$ alkoxcarbonyl such as methoxcarbonyl, ethoxcarbonyl and t-butoxcarbonyl—whereby t-butoxcarbonyl is preferable; and Y is a coupling moiety selected from the group consisting of carboWl, amino, isocyanate, isothiocyanate, imidate, maleimide, chlorocarbonyl, chlorosulfonyl, succinimidyloxcarbonyl, haloacetyl, and $C_{1-10}$ N-alkoxcarbamoyl—whereby N-methoxlcabamoyl is preferable.

Figure 3:
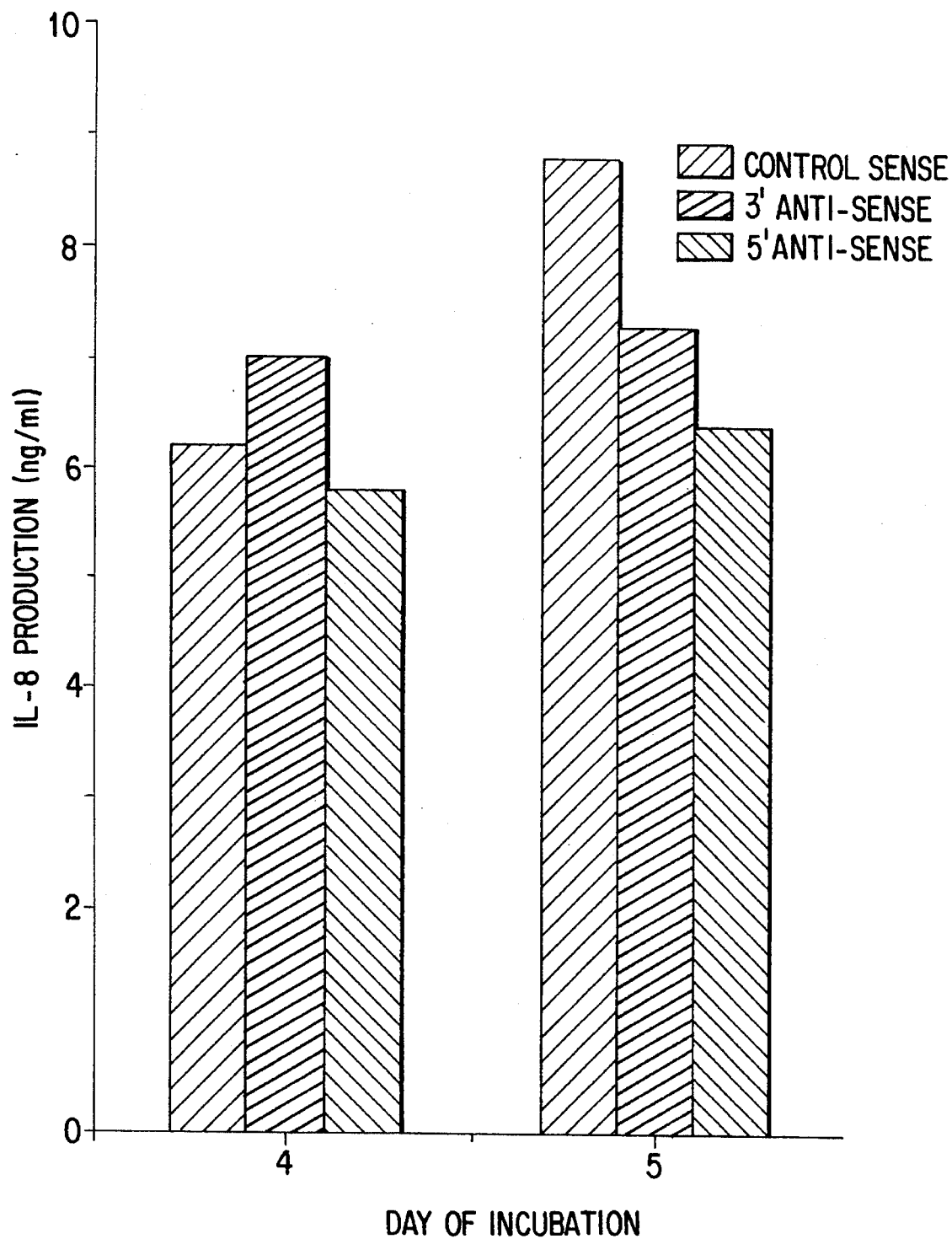
FIG. 3 is a graph showing IL-8 production in antisense oligonucleotidesto MCP-1 treated MLR cultures.

In another preferred embodiment of the present invention, antisense MCP-1 or a molecule having sense MCP-1 interactive capability is conjugated with the ligand illustrated in FIG. 3,

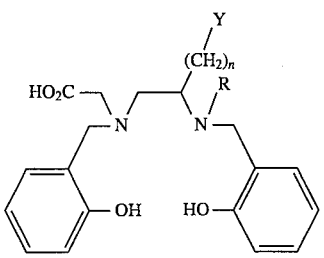

FIG. 3 wherein n varies from 1 to 10, and Y is a coupling moiety selected from the group consisting of carboxyl, amino, isocyanate, isothioganate, imidate, maleimide, chlorocarbonyl, chlorosulfonyl, succinimidyloxycarbonyl, haloacetyl, and $C_{1-10}$ N-alkoxycarbamoyl such as N-methoxycarbamoyl and t-butoxycarbamonyl—whereby t-butoxycarbamonyl is preferable; and R is selected from the group consisting of hydrogen and $C_{1-10}$ alkyl such as methyl and t-butyl—whereby t-butyl is preferable.

Figure 4:
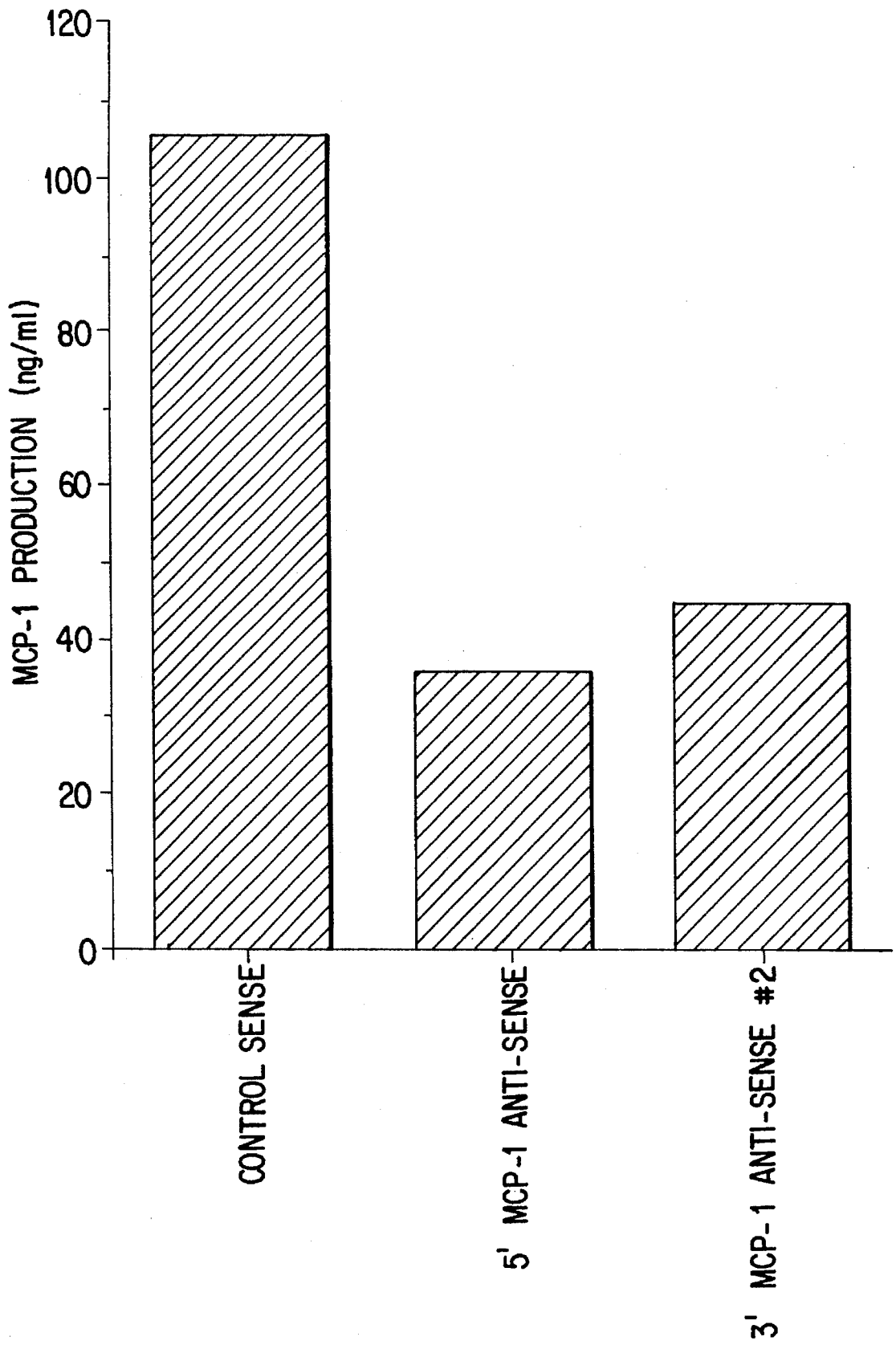
FIG. 4 is a graph showing MCP-1 production in PHA-stimulated peripheral blood mononuclear cells with and without the presence of antisense oligonucleotide to MCP-1 constructs.

In another preferred embodiment, the antisense MCP-1 or a molecule having sense MCP-1 interactive capability can be conjugated with the metal complex illustrated in FIG. 4

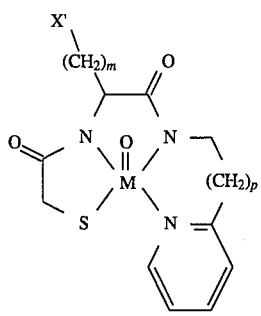

FIG. 4 wherein m is a whole number less than eleven and more preferably 3; p is either 0 or 1; X' is a coupling moiety selected from the group consisting of carboxyl, amino, isocyanate, isothiocyanate, imidate, maleimide, chlorocarbonyl, chlorosulfonyl, sucininimidyloxycarbonyl, haloacetyl and $C_{1-10}$ N-alkoxycarbamoyl such as N-methoxycarbamoyl and t-butoxycarbamoyl—whereby t-butoxycarbamoyl is preferable and M is a radionuclide suitable for diagnostic imaging or therapeutic use such as technetium, rhenium, copper, cobalt, indium, gallium, samarium, yttrium and holmium.

Figure 5:
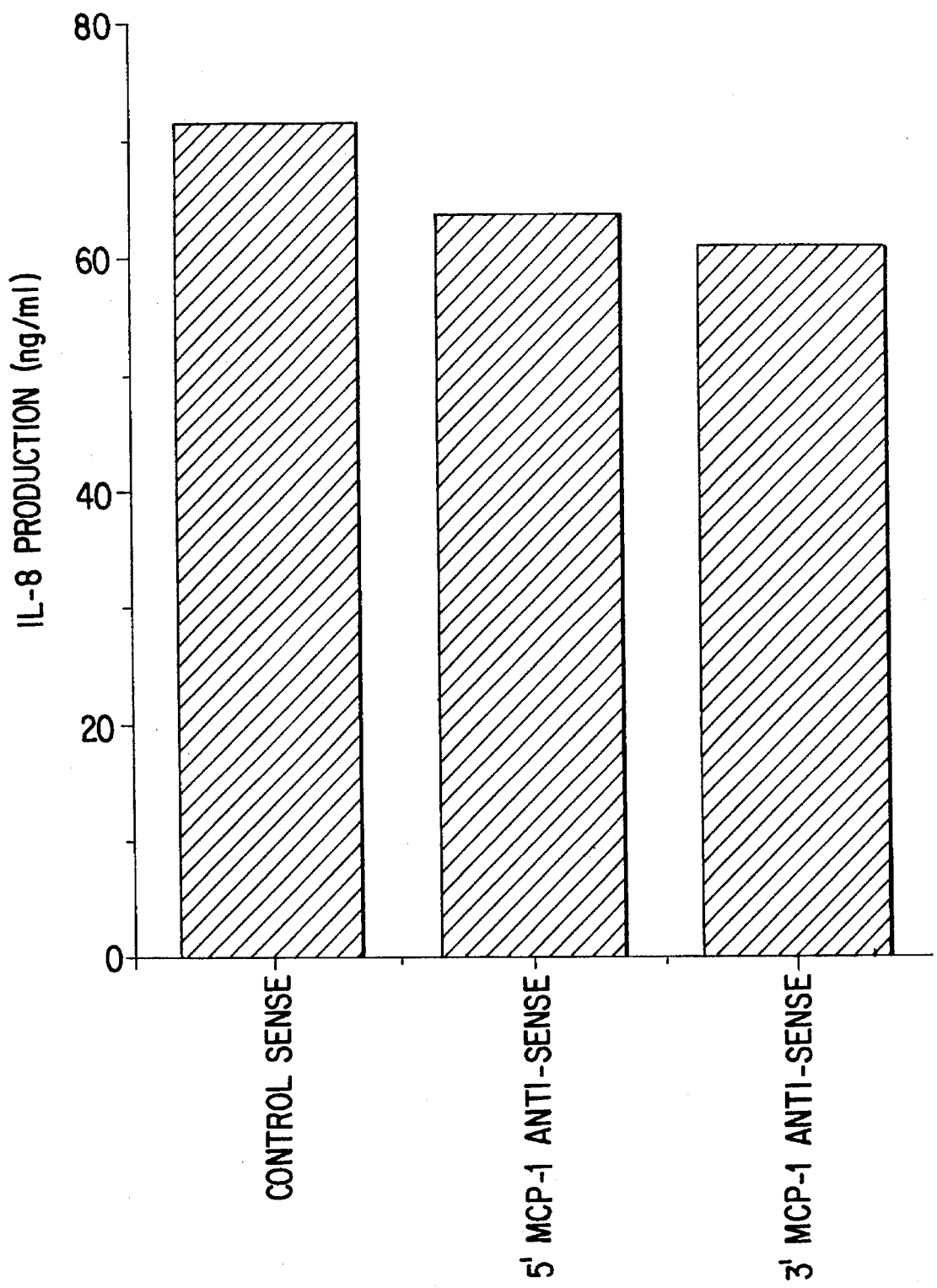
FIG. 5 is a graph showing IL-8 production in PHA-stimulated peripheral blood mononuclear cells with and without the presence of antisense oligonucleotidesto MCP-1 constructs.

In another preferred embodiment, the antisense MCP-1 or a molecule having sense MCP-1 interactive capability can be conjugated with a metal complex as illustrated in FIG. 5 wherein Y' and n are defined the same respectively as Y and n in FIG. 3 and M is defined the same as M in FIG. 4.

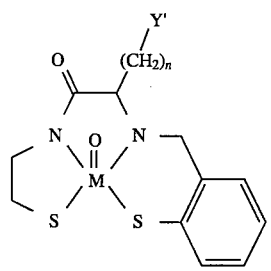

FIG. 5

Figure 6:
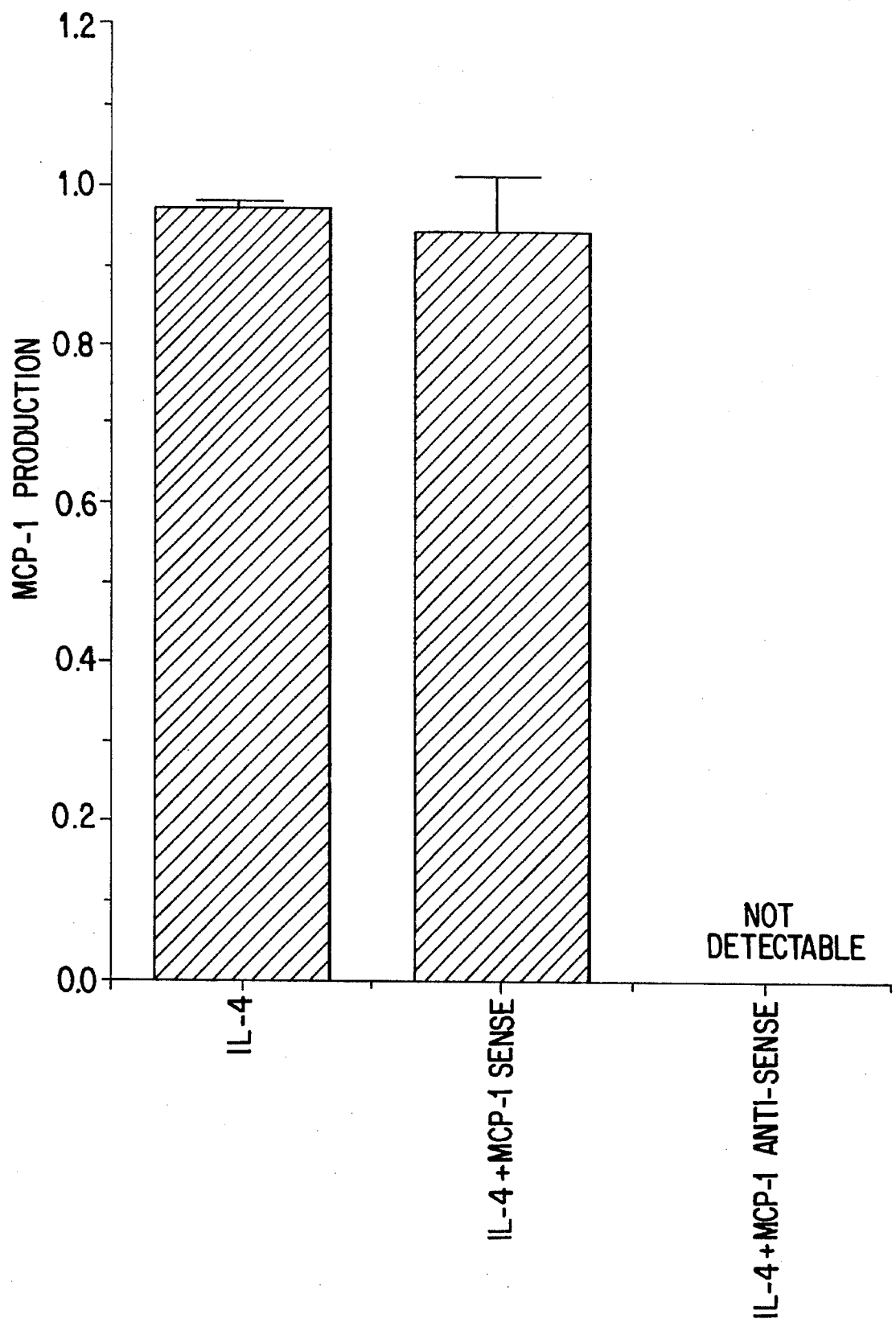
FIG. 6 is a graph showing MCP-1 production in murine smooth muscle cells treated with IL-4, IL-4 plus sense oligonucleotide to MCP-1, or IL-4 plus antisense oligonucleotidesto MCP-1.

In another preferred embodiment, the antisense MCP-1 or a molecule having sense MCP-1 interactive capability can be conjugated with a metal complex as shown in FIG. 6.

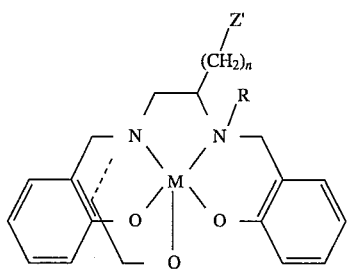

FIG. 6 wherein Z', q and R are defined the same respectively as Y, n and R of FIG. 3 and M is defined the same as M in FIG. 4.

In another preferred embodiment, the antisense MCP-1 or a molecule having sense MCP-1 interactive capability can be conjugated with a metal complex as shown in FIG. 7.

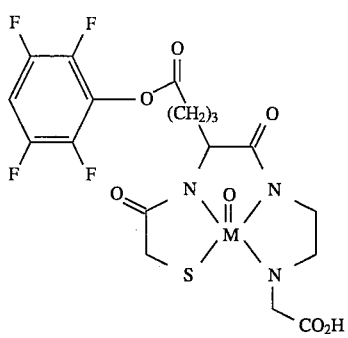

FIG. 7 wherein M is defined the same as M in FIG. 4.

Common esters which have been found useful in this labelling technique are o- and p- nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, thiophenyl, tetrafluorothiophenyl, o-nitro-p-sulfophenyl, N-hydroxyphthalimide and the like. For the most part, the esters will be formed from the reaction of the carboxylate with an activated phenol, particularly, nitro-activated phenols, or a cyclic compound based on hydroxylamine.

The advantages of using sulfur protecting groups include the fact that a separate step for removal of the sulfur-protective group is not necessary. The protecting groups are displaced from the compound during the labelling in what is believed to be a metal-assisted acid cleavage: i.e., the protective groups are displaced in the presence of a radionuclide at an acid pH and the radionuclide is bound by the chelating compound. The radiolabeling procedure thus is simplified, which is a significant advantage when the chelating compounds are to be radiolabelled in a hospital laboratory shortly before use. Additionally, another advantage of the present invention is that the basic pH conditions and harsh conditions associated with certain known radiolabeling procedures or procedures for removal of other sulfur protected groups are avoided. Thus, base-sensitive groups on the chelating compounds survive the radio-labelling step intact. Suitable sulfur-protecting groups, when taken together with the sulfur atom to be protected, include hemithioacetal groups such as ethoxyethyl, tetrahydrofuranyl, methoxymethyl, and tetrahydropyranyl. Other suitable sulfur protecting groups are $C_{1-20}$ acyl groups, preferably alkanoyl or benzoyl. Other possible formulas for the chelating compounds are described in U.S. Pat. No. 4,965,392 incorporated herein by reference.

Synthesis of the radionuclide bifunctional chelate and subsequent conjugation to antisense MCP-1, or a derivative thereof, can be performed as described in U.S. Pat. No. 4,965,392 incorporated herein by reference and related technologies as coveredby U.S. Pat. Nos. 4,837,003, 4,732, 974 and 4,659,839, each incorporated herein by reference.

After purification, the radiolabelled antisense MCP-1, or derivatives thereof, may be injected into a patient for therapeutic use or even diagnostic imaging depending on the radionuclide used. The radiolabelled antisense MCP-1 compound of the present invention is capable of radiotherapeutic use or reliably visualizing areas of potential restenosis within minutes post-injection. The antisense MCP-1 peptide when radiolabelled with the Re-186 or Re-188 triamide thiolate bifunctional chelate is particularly efficacious as an in vivo radiotherapeutic agent for areas of restenosis.

Still another embodiment of the present invention is the introduction of an antisense oligonucleotide or the gene for the synthesis of antisense MCP-1 oligonucleotide into individual vascular smooth muscle cells in area(s) of vascular injury.

When introducing this antisense MCP-1 gene into the vascular smooth muscle cells, replication of the antisense MCP-1 is aided byplacing it under the control of a tissue specific promoter such as the smooth muscle alpha actin promoter to prevent life-threatening vascular restenosis.

Such introduction is affected by infusion with a high concentration of oligonucleotide into the smooth muscle tissues with a balloon infusion catheter. This typically requires high pressure(s) (greater than 4 atmospheres) and high concentrations of oligonucleotides (greater than 12.5 micrograms per milliliter) and is aided by agents which help to increase the solubility of membranes such as lipid rich liposomes.

If based on RNA or DNA so as to bind to MCP-1 mRNA and prevent translation, the sequence to be introduced is derived from the RNA and DNA sequences previously given on pages 5 and 6.

It is important to note that effective inhibition of translation need not require the entire sequence. Appropriate specificity and ability to inhibit may be conferred with a sequence of approximately 15 to 30 nucleotides.

As noted above, the cysteine cysteine (CC) motif is a common feature characteristic of this family of chemokines and maintenance of this motif is a critical factor in preservation of biological activity. Therefore nucleotide sequences which would inhibit cysteine cysteine (CC) translation with preservation of specificity are particularly effective. For example the antisense RNA construct 5'- CAG UGG AGC ACA AUA UUG -3' (SEQ ID NO:6), or the DNA construct 5'- CAG TGG ACG ACA ATA TTG -3' (SEQ ID NO:9).

In a further embodiment of this invention, therapeutic effects of ant±sense oligonucleotides upon potentially proliferating smooth muscle cells are achieved by radiolabelling the ant±sense MCP-1 oligonucleotide with a suitable isotope such phosphorous 32 or phosphorous 33.

Each of the embodiments of the present invention are described in still greater detail in the illustrative examples which follow:

EXAMPLE 1

A solution of antisense MCP-1 peptide, or derivatives thereof, (0.01 mmol) in 2 mL of carbonate/bicarbonate buffer at pH 8.5±0.5 is treated with a solution of 0.1 mmol of the ligand illustrated in FIG. 1 (wherein m=2, p=1, $PG_1$ is benzoyl, and X is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired ant±sense MCP-1 conjugate.

EXAMPLE 2

A solution of ant±sense MCP-1 peptide, or derivatives thereof, (0.01 mmol) in 2 mL of carbonate/bicarbonate buffer at pH 8.5±0.5 is treated with a solution of 0.1 mmol of the ligand illustrated in FIG. 2 (wherein n=2, $PG_2$ and $PG_3$ are benzoyl, and Y is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired antisense MCP-1 conjugate.

EXAMPLE 3

A solution of antisense MCP-1 peptide, or derivatives thereof, (0.01 mmol) in 2 mL of carbonate/bicarbonate buffer at pH 8.5±0.5 is treated with a solution of 0.1 mmol of the ligand illustrated in FIG. 3 (wherein q=4, and Z is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired antisense MCP-1 conjugate.

EXAMPLE 4

To 100 uL of a solution containing 5 mg of sodium gluconate and 0.1 mg of stannous chloride in water, 500 ul of 99m-Tc04 (pertechnetate) is added. After incubation at room temperature for about 10 minutes, a solution of 500 uL of the antisense MCP-1 poiypeptide, or derivatives thereof, conjugates (1 mg/mL in 0.1M carbonate/bicarbonate buffer, pH 9.5) as described in Examples 1 or 2 is then added and the entire mixture is incubated at 37° C. for about 1 hour. The desired labelled peptide is separated from unreacted 99mTc-gluconate and other small molecular weight impurities by gel filtration chromatography (Sephadex G-50) using phosphine buffered physiological saline, (hereinafter PBS), 0.15M $NaC_1$, pH 7.4 as eluent.

EXAMPLE 5

A mixture of gentisic acid (25 mg), inositol (10 mg), and the antisense MCP-1 polypeptide, or derivatives thereof, conjugate (500 uL , 1 mg/mL in water) was treated with In-111 indium chloride in 0.05M HCl. The solution was allowed to incubate at room temperature for about 30 minutes. The desired labelled peptide is separated from unreacted In-111 indium salts and other small molecular weight impurities by gel filtration chromatography (Sephadex G-50) using phosphine buffered physiological saline, (PBS), 0.15M NaCl as eluent.

EXAMPLE 6

Antisense RNA or DNA or a derivative thereof for purposes of inhibition of translation is prepared by oligonucleotide synthesis, suspended to a concentration of between 10 and 500 micrograms per milliliter in 10mM. Tris chloride with 1mM ethylenediaminetetraacetic acid (EDTA) and infused into the lesion using a balloon infusion catheter at pressures of four to eight atmospheres. Contact time should be in the range of 5 to 30 minutes. If it is desired to radiolabel the preparation with phosphorus-32 or phosphorus-33 to increase therapeutic effect, phosphorus-32 or phosphorus-33 labeled nucleotides are added by nick translation in the case of DNA or by templated synthesis in the case of RNA.

EXAMPLE 7

Antisense DNA or a derivative thereof for purposes of inhibition of MCP-1 synthesis by inhibition of transcription by self replication within smooth muscle cells is prepared by introduction of such DNA sequences into a plasmid (a circular piece of DNA) consisting of a smooth muscle actin promoter coupled to antisense DNA to MCP-1 and appropriate start and stop signals. This plasmid is introduced into smooth muscle cells by using a balloon infusion catheter. The plasmid DNA is suspended to a concentration of between 10 and 100 micrograms per milliliter in Tris chloride EDTA (10 mM, 1 mM ETDA) (TE) and is infused at a pressure of between 4 and 8 atmospheres. Infusion time varies between 5 and 30 minutes.

After the antisense MCP-1 polypeptide, oligonucleotide or a derivative thereof is prepared and optionally labelled according to the procedure described above, the compound is used with a pharmaceutically acceptable carrier in a method of performing therapy or radiotherapy or a method of performing a diagnostic imaging procedure using a gamma camera or like device. These procedures involve injecting or administering, for example by means of a balloon injector catheter, to a warm-blooded animal an effective amount of the present invention and then in the case of diagnostic use, exposing the warmblooded animal to an imaging procedure using a suitable detector, e.g. a gamma camera. Images are obtained by recording emitted radiation of tissue or the pathological process in which the radioactive peptide or oligonucleotide has been incorporated, which in the present case are potential sites of restenosis, thereby imaging at least a portion of the body of the warm-blooded animal. Pharmaceutically acceptable carriers for either diagnostic or therapeutic use include those that are suitable for injection or administration such as aqueous buffer solutions, e.g. tris (hydroxymethyl)aminomethane (and its salts), chloride phosphate, citrate, bicarbonate, etc., sterile water for injection, physiological saline, and balanced ionic solutions containing chloride and/or bicarbonate salts of normal blood plasma cations such as $Ca^{2+}$, $Na^+$, $K^+$, and $Mg^{2+}$. Other buffer solutions are described in *Remington's Practice of Pharmacy*, 11th edition, for example on page 170. The carriers may contain a chelating agent, e.g. a small amount of ethylenediaminetetraacetic acid (EDTA), calcium, disodium salt, or other pharmaceutically acceptable chelating agents.

The concentration of the labelled or unlabelled peptide and the pharmaceutically acceptable carrier, for example in an aqueous medium, varies with the particular field of use. A sufficient amount is present in the pharmaceutically acceptable carrier in the present invention when satisfactory visualization of areas of vascular injury is achievable or satisfactory therapeutic results are achievable.

The composition is administered to the warm-blooded animals so that the composition remains in the living animal for about six to seven hours, although shorter and longer residence periods are normally acceptable.

The antisense MCP-1 compounds of the present invention or antisense MCP-1 derivative thereof, prepared as described herein, provide means of in vivo therapeutic, radiotherapeutic or diagnostic imaging of areas of potential restenois.

EXAMPLE 8

A mixed lymphocyte reaction (MLR) system was set up in 96-well flat-bottom tissue culture plates for proliferative studies and in 6-well plates for cytokine analysis. Responder cells were mixed 1:1 with stimulator cells in a total volume of 200 µl for 96-well plates and 1 ml for 6-well plates. RPMI 1640 growth media (Gibco) supplemented with 1 mM L-Glu, 10 mM HEPES buffer (Gibco), antibiotics streptomycin and penicillin, and 10 % fetal calf serum was used in the assay. Dilution studies of both the responder and stimulator cells determined that a 1:1 ratio provided optimal proliferative response. Cells were cultured at 37° C., $10^5$ cells/well for proliferative responses and $3 \times 10^6$ cells/well for cytokine elicitation. For determination of proliferation, cultured cells were pulsed with 0.5 µCi of $^3$-H-thymidine 12–18 hours prior to harvest on day 6. Cells were harvested and $^3$H-thymidine incorporation determined by scintillation counting. For cytokine determination, culture supernatants were harvested from 35 mm plates, centrifuged and stored at −20° C. until cytokine concentrations were assessed by ELISA. Preliminary studies were performed to determine the best responder and stimulator donors for the MLR assays.

The proliferative studies and cytokine analyses were done with oligonucleotides which were:
1) ANTISENSE TO HUMAN 5' MCP-1:
   5'-ACT-TCT-GCT-TGG-GGT-CAG-CAC-AGA-TCT-CC-3' (SEQ ID NO:8);
2) ANTISENSE TO HUMAN 3' MCP-1:
   5'-GCT-TCA-GTT-TGA-GAA-TTG-GAT-GTT-TCT-GG-3' (SEQ ID NO:9); or
3) ANTISENSE TO RAT 5'-MCP-1:
   5'-AAG-CGT-GAC-AGA-GAC-CTG-CAT-AGT-GGT-GG-3' (SEQ ID NO:10).

Results of the proliferative studies using 96-well plates are shown in FIG. 2, and results of the cytokine analyses are shown in FIGS. 1 and 3–6.

FIG. 1 demonstrates that the addition of two different antisense constructs to human MCP-1 added to the mixed lymphocyte reaction described above blocked normal production of MCP-1 that occurs at day 4 and 5 in this reaction.

FIG. 2 represents a control which demonstrates that the proliferative response, an endpoint of the mixed lymphocyte reaction, was not effected by the different antisense constructs to human MCP-1.

FIG. 3 represents an additional control demonstrating that the production of another cytokine, Interleukin-8 (IL-8), generated during the mixed lymphocyte reaction, was not effected by the different antisense constructs to human MCP-1. IL-8 production proceeds normally at 4 and 5 days in the mixed lymphocyte reaction.

FIG. 4 demonstrates that the two antisense constructs to human MCP-1 blocks the production of MCP-1 in another biological system used to generate MCP-1. In this study isolated human mononuclear cells were challenged with phytohemagglutinin (PHA), a stimulus for MCP-1 production. This PHA study was established using isolated human peripheral blood mononuclear cells challenged with 10 µg/ml of PHA±antisense constructs to human MCP-1 and supernatants harvested 24 hours later.

FIG. 5 represents a control for the PHA study described above, showing that IL-8 cytokine was not effected by antisense constructs to human MCP-1.

FIG. 6 demonstrates that cultured rat smooth muscle cells, when stimulated with interleukin-4, can generate MCP-1, and the addition of the antisense construct to rat MCP-1 can inhibit the production of murine MCP-1.

The oligonucleotides of the present invention are capable of inhibiting production of MCP-1 by cells of a warm-blooded animals, which cells are selected from the group consisting of mononuclear cells (including lymphocytes, monocytes and macrophages) and smooth muscle cells.

After consideration of the above specification, it will be appreciated that many improvements and modifications in the details may be made without departing from the spirit and scope of the invention. It is to be understood, therefore, that the invention is in no way limited, except as defined by the appended claims.

We claim:

1. A composition comprising an antisense MCP-1 oligonucleotide selected from the group consisting of 5'-ACTTCTGCTTGGGGTCAGCACAGATCTCC-3' (SEQ ID NO:8) and 5'-GCTTCAGTTTGAGAATTGGATGTTTCTGG-3' (SEQ ID NO:9), which composition inhibits MCP-1 production by human cells in vitro, said cells being selected from the group consisting of human mononuclear cells and human smooth muscle cells.

2. The composition of claim 1, wherein said human mononuclear cells are selected from the group consisting of lymphocytes, monocytes, and macrophages.

3. A method for inhibiting MCP-1 production by human cells in vitro, said cells being selected from the group consisting of human mononuclear cells and human smooth muscle cells, which method comprises contacting said cells with an MCP-1 production-preventing effective amount of an antisense oligonucleotide so as to inhibit MCP-1 production by said cells, wherein said antisense MCP-1 oligonucleotide is selected from the group consisting of 5'-ACTTCTGCTTGGGGTCAGCACAGATCTCC-3' (SEQ ID NO: 8) and 5'-GCTTCAGTTTGAGAATTGGATGTTTCTGG-3' (SEQ ID NO: 9).

4. The method of claim 3, wherein said human mononuclear cells are selected from the group consisting of lymphocytes, monocytes, and macrophages.

5. An antisense MCP-1 oligonucleotide selected from the group consisting of 5'-ACTTCTGCTTGGGGTCAGCACAGATCTCC-3' (SEQ ID NO:8) and 5'-GCTTCAGTTTGAGAATTGGATGTTTCTGG-3' (SEQ ID NO:9).

6. The composition of claim 1, wherein said antisense MCP-1 oligonucleotide is labelled with Phosphorus-32 or Phosphorus-33.

7. The method of claim 3, wherein said antisense MCP-1 oligonucleotide is labelled with Phosphorus-32 or Phosphorus-33.

* * * * *